United States Patent [19]
Kleiner

[11] 3,943,170
[45] Mar. 9, 1976

[54] PROCESS FOR THE PREPARATION OF HALO-METHYLPHOSPHINIC ACID HALIDES
[75] Inventor: Hans-Jerg Kleiner, Bad Soden, Taunus, Germany
[73] Assignee: Hoechst Aktiengesellschaft, Frankfurt am Main, Germany
[22] Filed: Nov. 30, 1973
[21] Appl. No.: 420,696

[30] Foreign Application Priority Data
Dec. 4, 1972  Germany............................ 2259241

[52] U.S. Cl. .............................. 260/543 P; 260/953
[51] Int. Cl.² ............................................ C07F 9/34
[58] Field of Search................................. 260/543 P

[56] References Cited
UNITED STATES PATENTS
3,188,281   6/1965   Briggeman et al.............. 260/543 P
3,200,145  10/1965   Lutz et al. ...................... 260/543 P Primary Examiner—Lorraine A. Weinberger
Assistant Examiner—Paul J. Killos
Attorney, Agent, or Firm—Curtis, Morris & Safford

[57] ABSTRACT

A process for the preparation of halo-methylphosphinic acid halides of the formula I

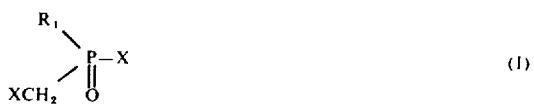

where $R_1$ is alkyl, aralkyl or aryl having from 1 to 18 carbon atoms, and X is halogen, which comprises reacting phosphinic acid derivatives of the formula II

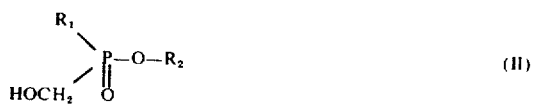

where $R_1$ is as defined above and $R_2$ is alkyl having from 1 to 18 carbon atoms optionally being substituted by halogen, hydrogen or a monovalent cation, with acid halides of the formula III

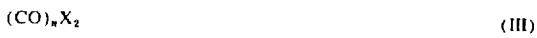

where $n$ is 1 or 2 and X is halogen.

6 Claims, No Drawings

PROCESS FOR THE PREPARATION OF HALO-METHYLPHOSPHINIC ACID HALIDES

The present invention relates to a process for the preparation of halo-methylphosphinic acid halides.

It is already known how to react methyl-dichlorophosphine with para-formaldehyde to form chloromethyl-methylphosphinic acid chloride. Yields of up to 70% of the theoretical yield were observed (L.C.D. Groenweghe et al., Am. Soc. 83, 1961, 1811). The reaction of methyldibromophosphine with paraformaldehyde gives a 16.1% yield of bromomethyl-methylphosphinic acid bromide (L. Maier, Helv. 46, 1963, 2667). Also phenyl-dichlorophosphine may be reacted in this manner (E.N. Cvetkov et al., Ž. obšč. Chim. 39, 1969, 1520). However, in these reactions there are formed various amounts of corresponding halo-methylphosphine anhydrides which decrease the yield. It was finally possible to react phosphorous trichloride with dimethyl ether at temperatures of from about 400°C to about 750°C, thus obtaining chloromethyl-methylphosphinic acid chloride with a 70% yield, relative to the dimethyl ether (German Auslegeschrift No. 1,768,617).

It has now been found to prepare halo-methylphosphinic acid halides of the formula I

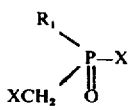  (I), where $R_1$ is alkyl, aralkyl or aryl having up to 18 carbon atoms, and X is halogen, with a good yield be reacting phosphinic acid derivatives of the formula II

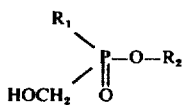  (II)

where $R_1$ is as defined above and $R_2$ is alkyl having from 1 to 18 carbon atoms optionally being substituted by halogen, hydrogen or a monovalent cation, with acid halides of the formula III $(CO)_nX_2$  (III)

where $n$ is 1 or 2 and X is halogen.

Preferred radicals $R_1$ are alkyl having from 1 to 10 carbon atoms, especially from 1 to 4 carbon atoms, above all methyl or ethyl; cyclo-alkyl having from 5 to 8 carbon atoms, especially cyclohexyl; furthermore aryl or aralkyl having from 6 to 18 carbon atoms, preferably from 6 to 10 carbon atoms, especially phenyl or phenylalkyl, such as phenethyl or especially benzyl.

The $R_2$ radical is either alkyl having from 1 to 18, especially from 1 to 10 carbon atoms and being optionally substituted by halogen; alkyl having from 1 to 4 carbon atoms, especially methyl, ethyl or chloroethyl which are preferred because of the easier distillation separation of the halo-alkyl formed. $R_2$ may also be hydrogen or a monovalent cation, preferably alkali or ammonium. For X being halogen, chlorine or bromine, especially chlorine, is preferred.

The phosphinic acid derivatives used as starting compounds may be obtained for example by reacting phosphonous acid monoesters with formaldehyde according to the process described in German Offenlegungsschrift No. 2 060 216.

Suitable starting compounds are for example hydroxymethyl-methylphosphinic acid, the sodium, potassium or ammonium salt thereof; hydroxymethyl-methylphosphinic acid methyl, isopropyl, butyl or isobutyl ester; hydroxymethyl-ethylphosphinic acid, hydroxymethyl-ethylphosphinic acid β-chloroethyl ester, hydroxymethyl-propylphosphinic acid isobutyl ester, hydroxymethyl-hexylphosphinic acid ethyl ester, hydroxymethyl-cyclohexylphosphinic acid butyl ester, hydroxymethyl-decylphosphinic acid, hydroxymethyl-decylphosphinic acid methyl ester, hydroxymethyl-benzylphosphinic acid methyl ester, hydroxymethyl-phenylphosphinic acid butyl ester.

As acid halides, there are used above all bromides and chlorides, such as phosgene, bromophosgene, oxalyl chloride or bromide. Preferably, phosgene is used.

The reaction may be carried out in the presence of solvents, for example methylene chloride, chloroform, carbon tetrachloride, benzene, toluene, xylene, chlorobenzene, dioxan, diethyl ether, diisopropyl ether. Especially when the alkali metal salts are used, the application of solvents is preferably recommended. It is not required that the salt dissolves in the solvents, a suspension is sufficient.

The reaction temperature is generally in a range of from about −20° to about +150°C, especially from 40° to 100°C. The reaction proceeds rapidly and, in the usual equipment, is complete within about 0.5 to 5 hours, depending on the temperature and, optionally, on the dimensions of the plant. It may be carried out under pressure, for example up to 5 or 10 atm/g, but preferably, it is carried out without pressure.

For carrying out the reaction of the invention, the reactants may be introduced into the reaction vessel in any desired sequence. Thus, for example, the phosphinic acid compound may be introduced first and the acid halide may then be added, or vice versa. When the reaction is carried out continuously, the reactants are advantageously introduced simultaneously in the desired ratio, preferably in a countercurrent when gaseous acid halides are used, for example in a column.

It is generally sufficient to use the reactants in stoichiometric amounts, that is, 2 moles of acid halide per mole of phosphinic acid derivative. Though an excess of acid halide, for example up to 2 or 5% which may be raised up to 10% in the case of small batches may also be employed, these excesses cause more expenditure for the work-up of the waste gas. Especially higher excesses may cause a decrease of the yield.

An advantage of the process of the invention resides in the fact that the by-products are gaseous or easily distillable. Only in the case where the alkali metal salts of phosphinic acids are used, alkali metal halides are obtained as solid by-products, but they can be easily separated under normal conditions, for example by suction-filtration. The process of the invention does not cause substantial corrosion problems; it may be carried out using all materials resistant under the reaction conditions, for example glass, ceramic, steel, steel alloys or nickel and nickel alloys.

Since the reaction proceeds with good to very good yields, it is possible in many cases where the phosphinic acid halides are only intermediates for further reactions to process these crude products directly, optionally in the solvent used. Otherwise, the isolation of the phosphinic acid halides may for example be carried out by distillation.

As intermediate products, for example for plant protection and flame retarding agents, the phosphinic acid halides of the invention are of great interest.

The following examples illustrate the invention.

EXAMPLE 1

Phosgene is introduced for 12.5 hours at room temperature and with vigorous agitation into 202 g (1.22 moles) of hydroxymethyl-methylphosphinic acid isobutyl ester, which raises the temperature to 60°C for a while. Subsequently, a vigorous current of nitrogen is passed through the reaction solution, and the reaction mixture is then distilled. 156.5 g of chloromethyl-methylphosphinic acid chloride having a boiling point of 76°C at 0.6 torr and a molecular weight of 147 are obtained, which corresponds to an 88% yield.

Analysis: Calculated: 48.3% of Cl. Found: 47.5% of Cl.

EXAMPLE 2

A. Preparation of hydroxymethyl-phenylphosphinic acid isobutylester 15 g of para-formaldehyde are added, at 70°C and with vigorous agitation, to 100 g (0.505 mole) of benzenephosphonous acid isobutyl ester. Agitation is continued for 1 hour at 75°–90°C. The reaction mixture is then cooled, stirred with water, and the organic phase is separated. The aqueous phase is extracted 2 times with chloroform, and the extract is added to the organic phase. After drying with sodium sulfate, distillation is carried out in a water jet vacuum at an interior temperature of up to 80°C. The residue is distilled in a thin layer evaporator at 0.1 torr and a distillation temperature of 190°C. Subsequently, the distillate is again distilled in a normal distillation apparatus. It is pure hydroxymethyl-phenylphosphinic acid isobutyl ester having a boiling point of 155°C at 0.3 torr.

B. Conversion to chloromethyl-phenylphosphinic acid chloride

Phosgene is introduced at room temperature with agitation into 59 g (0.259 mole) of hydroxymethyl-phenylphosphinic acid isobutyl ester. The temperature rises to 50°C. The reaction mixture is maintained at this temperature for 2.5 hours, subsequently, the introduction of phosgene is continued at 100°C for 3 hours. Distillation is carried out in a water jet vacuum at an interior temperature of up to 80°C, and the residue is distilled at 0.4 torr and a distillation temperature of from 120° to 130°C. 42 g of chloromethyl-phenylphosphinic acid chloride are obtained, having a melting point of 54°C and a molecular weight of 209, which corresponds to a yield of 78% of the theoretical yield.

Analysis: Calculated: 34.0% of Cl. Found: 33.8% of Cl.

What is claimed is:

1. A process for the preparation of a halomethylphosphinic acid halide of the formula

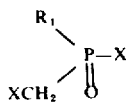

in which $R_1$ is alkyl of from 1 to 18 carbon atoms, cycloalkyl of from 5 to 8 carbon atoms phenyl or phenylalkyl of 7 to 10 carbon atoms and X is halogen, which comprises reacting a phosphinic acid derivative of the formula

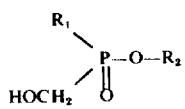

in which $R_1$ is as defined above and $R_2$ is hydrogen, a monovalent cation, or alkyl of from 1 to 18 carbon atoms optionally substituted by halogen, with a reactive acid halide of the formula

in which $n$ is 1 or 2 and X is halogen

2. The process as defined in claim 1, wherein $R_1$ is alkyl of from 1 to 10 carbon atoms, cycloalkyl of from 5 to 8 carbon atoms, phenyl or phenylalkyl of from 7 to 10 carbon atoms; X is chlorine; $R_2$ is hydrogen, an alkali or ammonium cation, or alkyl of from 1 to 10 carbon atoms optionally substituted by halogen, and phosgene is used as the reactive acid halide.

3. The process as defined in claim 2 wherein $R_1$ is alkyl of from 1 to 4 carbon atoms, cyclohexyl, phenyl or benzyl and $R_2$ is hydrogen, sodium, potassium, ammonium or alkyl of from 1 to 4 carbon atoms optionally substituted by chlorine.

4. The process as defined in claim 1, which comprises carrying out the reaction at a temperature of from −20° to +150°C.

5. The process as defined in claim 4, which comprises carrying out the reaction of a temperature of from 40° to 100°C.

6. A process as defined in claim 1, which comprises carrying out the reaction in the presence of solvents.

* * * * *